United States Patent [19]

Auditore-Hargreaves

[11] Patent Number: 4,479,895

[45] Date of Patent: Oct. 30, 1984

[54] IMMUNOGLOBULIN HALF-MOLECULES AND PROCESS FOR PRODUCING HYBRID ANTIBODIES

[75] Inventor: Karen Auditore-Hargreaves, Wilmington, Del.

[73] Assignee: E. I. Du Pont de Nemours and Company, Wilmington, Del.

[21] Appl. No.: 374,971

[22] Filed: May 5, 1982

[51] Int. Cl.³ .................... C07G 7/00; A61K 39/395
[52] U.S. Cl. .................................. 260/112 B; 424/85
[58] Field of Search ...................... 260/112 B; 424/85

[56] References Cited

U.S. PATENT DOCUMENTS

| | | | |
|---|---|---|---|
| 3,995,018 | 11/1976 | Sjöquist | 260/112 B |
| 4,059,571 | 11/1977 | Tomibe et al. | 260/112 B |
| 4,160,763 | 7/1979 | Muller | 260/112 B |
| 4,302,384 | 11/1981 | Funatsu et al. | 260/112 B |
| 4,355,023 | 10/1982 | Ehrlich et al. | 260/112 B |
| 4,360,457 | 11/1982 | Ono et al. | 260/112 B |

OTHER PUBLICATIONS

Hong et al., J. Biol. Chem., 240, 3883 (1965).
Luedtke et al., Biochemistry, 19, 1182 (1980).
Peabody et al., Biochemistry, 19, 2827 (1980).
Sears et al., Biochemistry, 16, 2031 (1977).
Bobrzecka et al., Immunology Letters, 2, 15 (1980).
Rivat et al., Eur. J. Immunol., 3, 537 (1973).
Virella, et al., Immunochemistry, vol. 10 pp. 213–217(1973), Cecil et al., Biochem. J. 1962(82), 401–406.
Williamson, et al., Biochem. J. 107 pp. 823–828 (1968).
Johnson, et al., Malec. Immunol. 18 pp. 181–188 (1981).
Wright et al., Eur. J. Immunol 8 pp. 309–314 (1980).

*Primary Examiner*—Howard E. Schain
*Attorney, Agent, or Firm*—G. A. Frank

[57] ABSTRACT

A process for preparing covalent hybrid antibodies is provided. These antibodies are obtained by the ordered covalent hybridization of intact immunoglobulin molecules. The generation of half-molecules from different IgG antibodies by reductive or S-sulfonation selective cleavage is followed by the ordered association of the different half-molecules. The pure covalent hybrid antibodies as new substances are also provided along with IgG half-molecules.

15 Claims, No Drawings

IMMUNOGLOBULIN HALF-MOLECULES AND PROCESS FOR PRODUCING HYBRID ANTIBODIES

DESCRIPTION

1. Technical Field

This invention relates to a process for preparing immunoglobulin half-molecules and more particularly to the selective rejoining of dissimilar half-molecules of IgG antibodies to form covalent hybrid antibodies.

2. Background Art

Hybrid antibodies of the IgG class are heterobifunctional antibodies having two binding sites for antigens, each site having been derived from a different immunoglobulin. Usually, each of the two binding sites recognizes a different antigen, but it is possible for both binding sites to bind the same antigen and to differ with respect to other properties, for example, idiotype.

The synthesis of hybrid antibodies has been achieved in low yields by means of reductive dissociation of each of two intact immunoglobulin molecules ($H_2L_2$), having different antigen-binding specificities, into half-molecules ($H_1L_1$), where H represents the heavy chain and L, the light chain of immunoglobulin, followed by reoxidation of a mixture of these half-molecules; see, for example, Hong, et al., J. Biol. Chem., Volume 240, 3883 (1965). This purely random reoxidation has the disadvantage of yielding a theoretical maximum of 50% of the desired hybrid product.

Luedtke, et al., Biochemistry, Volume 19, 1182 (1980), describe the preparation of a hybrid antibody, in a mixture with the parent immunoglobulin molecules, resulting from the random reassociation of two immunoglobulin half-molecules. After removal of one parent immunoglobulin, the resulting immunoglobulin population contained approximately 46% of the desired hybrid antibody. No further purification to obtain the desired hybrid antibody was carried out.

Heterologous recombination of immunoglobulin light chains to form dimers has been carried out by means of a nucleophilic displacement reaction; see Peabody, et al., Biochemistry, Volume 19, 2827 (1980). Immunoglobulin light chains are synthesized in abnormally high concentrations in certain diseased patients, e.g., multiple myeloma patients, and are excreted into the urine. Protein purification carried out on such samples led to light chain dimers. Splitting of light chain dimers from one source by sulfitolysis of the interchain disulfide bond afforded a thiosulfate derivative. Light chain dimers from a second source were split by reduction of the interchain disulfide bond to yield the corresponding sulfhydryl compound. Admixture of these two monomeric species, in turn, led to the formation of heterologous light chain, disulfide-linked dimers by a nucleophilic displacement reaction. Yields of 80 to 100% were reported. These light chain dimers are covalently bonded by a single disulfide bond and are not immunologically active. Native immunoglobulin molecules, on the other hand, have more than one disulfide bond and the specific cleavage of the inter-heavy chain disulfide bond(s) to form the desired half-molecule is difficult.

The reduction of the inter-heavy chain disulfide bond(s) of intact IgG molecules to form half-molecules by chemical means is difficult without concurrently causing some reduction of heavy-light chain disulfide bond(s) as well; see Sears, et al., Biochemistry, Volume 16, 2031 (1977). Limited proteolysis of IgG to yield F(ab')$_2$ fragments has been thought to be necessary to selectively enhance the susceptibility of the inter-heavy chain bond(s) to chemical attack; see Bobrzecka, et al., Immunology Letters, Volume 2, 15 (1980). Such limited proteolysis yields a mixture of products requiring subsequent chromatographic purification.

Rivat, et al., Eur. J. Immunol., Volume 3, 537 (1973), describe a procedure by which the inter-heavy chain disulfide bonds of immunoglobulins are reduced by electrochemical means to yield half-molecules with free sulfhydryl groups. These half-molecules, however, could not be isolated because they were subject to spontaneous reoxidation and homologous reassociation. An alkylation process was used for the analysis of these half-molecules but even this reaction had to be carried out in a nitrogen atmosphere.

There is a need for an efficient method for the production of IgG half-molecules from intact IgG. There is also a need for a practical method for the synthesis of covalent hybrid antibodies from such half-molecules.

DISCLOSURE OF THE INVENTION

The half-molecules of this invention are substantially pure immunoglobulin heavy chain-light half-molecules having the structure R—S—X, where R is $H_1L_1$ and X is either hydrogen (H) or $SO_3^\ominus$. They are prepared by selectively cleaving an immunoglobulin molecule into its heavy chain-light chain half-molecules by sulfitolysis or by reduction of the inter-heavy chain disulfide linkage.

The antibodies of this invention are substantially pure covalent hybrid antibodies consisting essentially of two different heavy chain-light chain half-molecules, wherein the first of the half-molecules provides a binding site for a first antigen and the second of the half-molecules provides a chemically different binding site for the first or a second antigen; and wherein the half-molecules are bonded to each other through disulfide linkage. These antibodies are prepared through the steps of:

(A) selectively cleaving a first immunoglobulin molecule which is an antibody to a first antigen into its heavy chain-light chain half-molecules by sulfitolysis of the inter-heavy chain disulfide bond to produce S-sulfonated half-molecule;

(B) selectively cleaving a second immunoglobulin molecule which is an antibody to the first or a second antigen into its heavy chain-light chain half-molecules by reduction of the inter-heavy chain disulfide bond to produce reduced half-molecules; and (C) combining the S-sulfonated half-molecules from step (A) with the reduced half-molecules from step (B).

DESCRIPTION OF THE INVENTION

The process of this invention comprises several different methods for the selective cleavage of the inter-heavy chain disulfide bond(s) of intact IgG to yield heavy chain-light chain half-molecules ($H_1L_1$), as well as the ordered recombination of dissimilar half-molecules thus obtained to yield covalent hybrid antibodies ($H_1^aL_1^aH_1^bL_1^b$). The dissimilar halves of the hybrid antibodies are held together by disulfide linkage. This process results in high yields of the desired product often without the need for purification. The two half-molecules provide two chemically different binding sites for either two different antigens or for the same antigen but at differing locations on the antigen.

The process of this invention is a multistep procedure. The first step in the process of this invention is the selective cleavage of the inter-heavy chain disulfide bond(s) of two different intact IgG molecules. The use of monoclonal antibodies is also contemplated. Half-molecules formed from the parent IgG molecules are then combined in such a manner as to favor disulfide-bond formation between dissimilar half-molecules.

Selective cleavage of the inter-H chain bond and the production of IgG half-molecules can be achieved in several ways. In one method, intact IgG if sulfitolyzed with sodium sulfite in the presence of 5,5'-dithiobis(2-nitrobenzoic acid), preferably in a buffered medium at room temperature under nitrogen, to yield S-sulfonated half-molecules of IgG. One of the two half-molecules of IgG which can be used in the hybrid-forming reaction is S-sulfonated in this manner.

In a second method, S-sulfonated half-molecules of IgG formed as described above are reacted with a thiol-containing reagent such as dithiothreitol, β-mercaptoethanol and β-mercaptoethylamine, preferably in a buffered medium containing strontium chloride, under nitrogen. Separation of the protein products of this reaction from the thiol reagent can be subsequently effected by gel filtration or dialysis. The protein products of this reaction are reduced half-molecules of IgG bearing free sulfhydryl group(s).

In a third method, intact IgG is first allowed to bind to a receptor, such as Protein A or antigen, covalently bound to a suitable support (e.g., agarose beads). A thiol-containing reagent such as dithiothreitol or β-mercaptoethanol is then reacted with the bound IgG (at room temperature, in a buffered medium, under nitrogen). The resultant bound IgG half-molecules having free sulfhydryl groups can then be dissociated from the support using a high-salt, low-pH buffer, and dialyzed against the same buffer to remove the thiol reagent.

The second of the two half-molecules of IgG which can be used in the hybrid-forming reaction is a free sulfhydryl-containing half-molecule prepared according to one of the methods described above.

The ordered hybridization of IgG molecules to provide hybrid antibodies having different antigen-binding specificites can be accomplished by different procedures. In one procedure, S-sulfonated half-molecules are derived from a first IgG by sulfitolysis as described above. The protein product (immunoglobulin half-molecules) can be separated from the other products of the sulfitolysis reaction by dialysis against a suitably buffered medium through which nitrogen is bubbled at room temperature. Sulfhydryl-containing half-molecules are derived from a second IgG by one of the methods described above. Removal of the thiol reagent, where one is present, can be accomplished without reoxidation of the protein either by gel filtration or by dialysis in a buffered medium of pH 5, containing, for example, ethylene diamine tetraacetic acid, which has been thoroughly degassed and through which nitrogen is bubbled. The two different populations of half-molecules generated by these methods are then combined in equimolar amounts and dialyzed under anaerobic conditions in a suitably buffered medium (containing strontium chloride or another alkali earth metal salt). A nucleophilic displacement reaction, shown below, affords the desired hybrid antibody product in which the dissimilar halves are joined together by disulfide linkage.

$$R-S-SO_3^- + R'-SH \rightarrow R-S-S-R' + HSO_3^-$$

where
R is $H_1^a L_1^a$ and
R' is $H_1^b L_1^b$

In another procedure of hybridization, S-sulfonated half-molecules are derived from a first IgG by sulfitolysis, as described above. Sulfhydryl-containing half-molecules are derived from a second IgG as described above in the third method for selective cleavage of the inter-H chain bonds. The bound IgG half-molecules, however, are not eluted from the support (such as antigen coated beads or Protein A immobilized on Sepharose gel) to which they are bound. Instead, the support is washed by suspending in a suitable buffer, followed by centrifugation, to remove the thiol reagent. The S-sulfonated half-molecules of the first IgG are then added to the bound sulfhydryl containing half-molecules of the second IgG in a suitably buffered medium, containing strontium chloride, and incubated at room temperature in an inert atmosphere. The hybrid antibodies so produced, formed on the support surface by nucleophilic displacement, can be eluted with a buffer containing an appropriate chaotropic agent (for example, high-salt concentration solution or surfactant).

The reaction products from each of the methods of selective cleavage and from the procedures for hybridization can be analyzed using the techniques described below.

Sodium dodecyl sulfate (SDS)-polyacrylamide gel electrophoresis (PAGE) under nonreducing conditions can be used to compare the electrophoretic mobilities of the unknown proteins or polypeptides to known proteins in order to estimate the molecular weights of the unknowns. This method permits the determination of the presence in reaction mixtures of individual heavy or light chains, half-molecules, or complete IgG molecules.

Isoelectric focusing in polyacrylamide gels can be used to separate proteins on the basis of differences in their isoelectric pH's, that is, the pH at which a protein has no net charge in a particular solvent. The presence of hybrid antibodies as different from either of the parent antibodies can be determined by this technique. This technique is more discriminating than SDS-PAGE.

Double diffusion in agar gel provides a method for detecting antigen binding by an antibody. Antigen and antibody placed in separate wells in the gel are allowed to diffuse toward each other. Binding of antigen by antibody results in a line of precipitate (insoluble antigen-antibody complexes) visible between the wells. Only bivalent antibodies will form precipitates with their antigens. Hybrid antibodies, which are monovalent with respect to each antigen, therefore, will not precipitate with either antigen.

Hybrid antibodies, prepared by the process of this invention, are useful in immunoassays requiring antibody recognition of two different antigens. In particular, they are useful in those circumstances in which the binding of a first antigen to the covalent hybrid antibody can modulate the binding of a second antigen to the hybrid antibody. The first antigen is an analyte of interest and the second antigen is an indicator such as an enzyme whose activity is modulated upon binding to the hybrid antibody. The simultaneous binding of both antigens to the hybrid antibody is inhibited by steric or ionic factors and thus the activity of the enzyme will be inversely proportional to the level of analyte in the biological fluid to be analyzed. Alternatively, the second antigen (indicator) is an aggregating substance whose binding to the covalent hybrid antibody modulates the aggregation of latex particles. Such homogeneous immunoassays employing covalent hybrid antibody produced by the process of this invention are described in a copending application, Ser. No. 374,970, filed May 5, 1982.

By analyte of interest in the biological sample is meant the substance whose concentration is desired to be determined. The biological sample can be a biological fluid such as whole blood, blood serum, blood plasma, saliva, cerebral spinal fluid or urine or can be cell and tissue extracts. The analyte is often a protein present in one of these biological fluids but also includes drugs, hormones, vitamins, enzymes, antibodies, polysaccharides, bacteria, protozoa, fungi, viruses, cell and tissue antigens and other blood cell or blood fluid substances.

The process of this invention is also useful in the preparation of monovalent antibody fragments, i.e., half-molecules ($H_1L_1$). There are several reports in the literature of the utility of monovalent antibody fragments such as Fab and Fab' fragments. Fab fragments can be generated from intact IgG by limited proteolysis with the enzyme papain; they are monovalent with respect to antigen binding but lack the $F_c$ region of IgG. Fab' fragments can be generated by reduction of the inter-H chain disulfide bond(s) of F(ab')$_2$ fragments which, in turn, can be derived from pepsin cleavage of intact IgG. Fab' fragments are also monovalent but also lack the $F_c$ region. Half-molecules synthesized by the process of this invention are monovalent with respect to antigen binding, contain reactive sulfhydryl or thiosulfate group(s), and retain the important $F_c$ region. Their synthesis is rapid and requires no purification steps.

EXAMPLE 1

Synthesis of a Hybrid Antibody

A. Preparation of S-sulfonated Half-Molecule

A commercially available IgG fraction from rabbit serum containing anti-horseradish peroxidase antibody (anti-HRP) was further purified by immunoaffinity chromatography on horseradish peroxidase-coupled agarose beads. The bound fraction containing anti-HRP was eluted from the affinity adsorbent with 2.5M sodium thiocyanate in phosphate-buffered saline (PBS). The PBS buffer consisted of 0.14M sodium chloride, 2 mM potassium chloride, 8 mM dibasic sodium phosphate, 1.5 mM dipotassium phosphate, and, optionally, 0.02% (w/v) sodium azide, at a pH of 7.4. The eluate was dialyzed against multiple changes of 0.1M borate, pH 8.5, containing 4 mM ethylene diamine tetraacetic acid (EDTA). The final concentration of the anti-HRP was adjusted to 2 mg/mL, assuming a 1 mg/mL solution of IgG to have an optical density of 1.4 at 280 nm.

To 0.5 mL (1 mg) of this purified anti-HRP was added 6.26 mg solid sodium sulfite and 0.5 mg solid 5,5'-dithiobis(2-nitrobenzoic acid) (DTNB). The reaction mixture was stirred in a nitrogen atmosphere for 3 hours at room temperature and was then dialyzed overnight at room temperature against 20 mM N-tris(hydroxymethyl)methyl-2-aminoethanesulfonic acid (TES) buffer, pH 6.5, containing 1 mM EDTA. The product was S-sulfonated rabbit anti-HRP half-molecules.

Analysis under nonreducing conditions of the S-sulfonated rabbit anti-HRP on discontinuous SDS-polyacrylamide gels showed a single band of apparent molecule weight of 75,000 Daltons, corresponding to the half-molecule $H_1L_1$. Upon reduction with β-mercaptoethanol (βME, 5% v/v), two bands of apparent molecular weights of 55,000 and 23,000 Daltons were seen, corresponding to free heavy (H) chains and free light (L) chains, respectively.

B. Preparation of a Reduced (SH) Half-Molecule

An Ig fraction was prepared from commercially available goat serum containing anti-glucose oxidase (anti-GO) by adding to the serum an equal volume of saturated ammonium sulfate, pH 7.0, in distilled water. This solution was stirred at room temperature for 30 minutes and was then centrifuged at 8000×g at 4° C. The supernatant liquid was decanted and the pellet was resuspended in saturated ammonium sulfate, centrifuged, and the supernatant liquid decanted again. The pellet was redissolved in half of the original serum volume of distilled water and the resultant solution dialyzed exhaustively against PBS. The dialyzed solution was then applied to protein A-coupled Sepharose CL-4B gel (available from Pharmacia) in a sintered glass funnel. Approximately 5 mL of gel was used per 2.5 mL of Ig fraction. The gel was washed with 20 volumes of PBS and the bound fraction containing IgG was eluted with one volume of 0.1M glycine, pH 3.0. The eluate was dialyzed exhaustively against PBS. The dialyzed solution was concentrated to a protein concentration of 2 mg/mL by ultrafiltration using an Amicon PM-30 membrane and its purity judged to be >95% by SDS-PAGE. This IgG fraction was then further purified by immunoaffinity chromatography on glucose-oxidase-coupled agarose beads. Elution of the anti-GO was performed as described above for anti-HRP. The final concentration was adjusted to 2 mg/mL.

To 1.0 mL (2 mg) of this purified goat anti-GO was added 1 mL of GO-coupled Sepharose 4B, prepared from CNBr-activated Sepharose 4B. The approximate ratio of GO to Sepharose was 2 mg/mL of wet gel. The antibody was incubated with the gel for one hour at room temperature with constant mixing. After this time, the gel was centrifuged in a clinical centrifuge and the supernatant withdrawn. The optical density of the supernatant was determined at 280 nm. Using a value of 1.4 for the optical density of 1 mg/mL solution of IgG, it was estimated that approximately 50% of the anti-GO antibody was bound to the gel. The gel was washed three times by suspension in 0.1M borate/4 mM EDTA, pH 8.5, followed by centrifugation and aspiration of the supernatant. After the final wash, the pellet was resuspended in an equal volume of 14 mM βME in 0.1M borate/4 mM EDTA, pH 8.5, and incubated with shaking for 30 minutes at room temperature under a blanket of nitrogen. The gel was separated from suspension by centrifugation, the supernatant aspirated, and the gel eluted with 0.1M glycine/4 mM EDTA, pH 3.0. The eluate was dialyzed overnight against 0.02M glycine/4 mM EDTA, pH 3.0, through which nitrogen was bubbled continuously. The product was reduced (SH) goat anti-GO.

Analysis by SDS-PAGE of the reduced goat anti-GO preparation under nonreducing conditions revealed a single major band of apparent molecular weight of 75,000 Daltons. Two minor bands (accounting for less than 10% by weight of the total protein) also appeared having apparent molecular weights of 55,000 and 23,000 Daltons, respectively. These three correspond, respectively, to half-molecules ($H_1L_1$), free H chains, and free L chains. Upon addition of βME (5% v/v), the 75,000 Dalton band was converted to the 55,000 and 23,000 Dalton bands, as expected.

C. Preparation of Hybrid Antibody

Equal amounts of the S-sulfonated rabbit anti-HRP and the reduced goat anti-GO were mixed and transferred to dialysis tubing. The resultant solution was dialyzed for 24 hours at room temperature against 20 mM TES, 1 mM EDTA, and 0.1M strontium chloride, pH 6.5, through which nitrogen was bubbled continuously. The mixture was then dialyzed against PBS for 24 hours.

Analysis of the dialyzed solution by SDS-PAGE under nonreducing conditions revealed a single major band of apparent molecular weight of 150,000 Daltons which, upon reduction (5% βME, v/v), yielded two bands of apparent molecular weights 55,000 and 23,000 Daltons, respectively. These three molecular weights correspond to the product covalent hybrid antibody, free H chains, and free L chains. (Less intense bands at 55,000 and 23,000 Daltons were detected under nonreducing conditions when the gels were overloaded. These bands probably represent the free H and free L chains generated during the reduction of anti-GO.)

The covalent hybrid antibody was further characterized by double diffusion in agar gel: when the parent antibodies, anti-HRP and anti-GO, were diffused against HRP and GO, respectively, precipitin bands were observed, while the hybrid antibody formed by the process of this invention from S-sulfonated anti-HRP and reduced anti-GO failed to form a precipitate with either HRP or GO. Also, when S-sulfonated anti-HRP was diffused against HRP or when reduced (SH) anti-GO was diffused against GO, no precipitin lines were formed confirming the monovalent nature of these half-molecules with respect to antigen binding. Precipitin lines were seen, however, when the hybrid antibody was diffused against either sheep anti-rabbit IgG or sheep anti-goat IgG, indicating the dual (hybrid) character of the antibody.

The hybrid antibody prepared above was still further analyzed by solid phase immunoprecipitation for its ability to bind an enzyme antigen. Twenty-five microliters of hybrid antibody was incubated for 1 hour at room temperature with 10 μL of glucose oxidase (1 mg/mL in PBS). 75 μL of a suspension of goat anti-rabbit IgG-coated latex beads (available from Bio-Rad) in PBS containing 1% ovalbumin (OVA) and 0.05% Triton X-100 (a nonionic surfactant available from Rohm and Haas Company) was added to the above and incubated, with shaking, for 1 hour at room temperature. The suspension was centrifuged and the pellet washed in the PBS/OVA/Triton X-100 buffer three times by centrifugation. After the final wash, the beads were resuspended in 500 μL of 0.1M glucose in PBS, 100 μL of o-phenylenediamine (OPD) (5 mM), and 10 μL of horseradish peroxidase (1 mg/mL in PBS). The formation of a color was monitored spectrophotometrically at 460 nm. Controls for this assay included the use of self-hybridized goat anti-glucose oxidase in place of the rabbit/goat hybrid antibody, and assays using either no antibody or no glucose oxidase.

The basis of color formation in this assay was as follows: the hybrid antibody was found to goat anti-rabbit IgG-coated beads by virtue of its rabbit (HRP binding) character. Glucose oxidase was precipitated by these beads only if hybrid antibody was present. (Presence of intact goat anti-glucose oxidase or of half-molecules of the same will not affect the assay, since these will not be precipitated by the goat anti-rabbit IgG-coated beads. This was verified by a control assay utilizing goat anti-glucose oxidase which has been hybridized with itself in a manner similar to that described in this Example.) After washing to remove any free glucose oxidase, glucose, OPD, and HRP were added. Glucose oxidase hydrolyzed glucose to yield $H_2O_2$, which served as the substrate for HRP. Color was generated only in the presence of glucose oxidase bound by the hybrid antibody (all free GO having been washed out).

When assayed as described, the hybrid antibody synthesized in this Example led to color formation. Elimination of the antibody or the glucose oxidase from the assay resulted in no color formation. When self-hybridized goat anti-glucose oxidase was substituted for the rabbit/goat hybrid, no color resulted. These results proved that the desired hybrid antibody product was obtained.

EXAMPLE 2

Preparation of IgG Half-Molecules Through Reduction with β-Mercaptoethanol of Immobilized Antibodies Protein A-Sepharose CL-4B gel was swollen in 0.1M borate/4 mM EDTA buffer, pH 8.5. To 50 μL of a 50% (v/v) suspension was added 100 μL of a 1 mg/mL solution of rabbit anti-horseradish peroxidase IgG. This was incubated for 1 hour at room temperature with constant agitation and then centrifuged. The supernatant liquid was aspirated and the pellet washed three times with 0.1M borate/4 mM EDTA buffer, pH 8.5. After the last wash, the pellet was resuspended in 100 μL of 14 mM β-mercaptoethanol in the same buffer and incubated under nitrogen for 15 minutes at room temperature. It was then centrifuged, the supernatant liquid aspirated, and the pellet washed three times with the borate/EDTA buffer. The pellet contained reduced half-molecules bound to the Protein A-Sepharose gel. The yield of the reduced rabbit anti-HRP half-molecules was 75%, 90% of which remained bound to the gel through the washing steps. The bound half-molecules can be utilized as is (see Example 3) or could be eluted from the gel by 0.1M glycine/1 mM EDTA buffer, pH 3.0. The product was characterized utilizing the procedures as described above.

EXAMPLE 3

Preparation of Hybrid Antibody

An equivalent weight of S-sulfonated goat anti-GO half-molecules, prepared as shown in Example 1, Part A, in 20 mM TES/1 mM EDTA/0.1M $SrCl_2$ was added to the pellet prepared in Example 2 above. The pellet was resuspended and agitated overnight at room temperature under nitrogen. The supernatant was then removed and the pellet was washed once with 20 mM TES/1 mM EDTA/0.1M $SrCl_2$ and twice more with TES/EDTA. The bound product IgG hybrid antibody as eluted with 0.1M glycine, pH 3.0, and dialyzed into PBS. The product was characterized utilizing the procedures described above.

EXAMPLE 4

Preparation of IgG Half-Molecules Through Reduction with β-Mercaptoethylamine

To 900 μL of rabbit IgG (2 mg/mL) was added 100 μL of 1M β-mercaptoethylamine in 20 mM TES/1 mM EDTA, pH 6.5. Incubation was carried out for 2 hours at 37° C., after which the sample was passed over Sephadex G-25 gel equilibrated in TES/EDTA. Approximately 80% of the IgG was converted to reduced half-molecules under these conditions. The remaining 20% was H-chain dimers and free L chains. The reduced half-molecules so produced can be utilized to produce covalent hybrid antibodies in accordance with Example 1, Part C. The product was characterized utilizing the procedures described above.

EXAMPLE 5

Alternate Synthesis of Covalent Hybrid Antibody

Goat anti-glucose oxidase, purified as described in Example 1, Part B, can be S-sulfonated as described for the rabbit anti-HRP in Example 1, Part A. After the dialysis step to remove excess DTNB, the reaction mixture can be adjusted to a concentration of 0.014M in βME and dialyzed overnight against a buffer containing 20 mM glycine, 4 mM EDTA, 0.1M SrCl$_2$, at a pH of 3.0. The solution can then be hybridized with the S-sulfonated rabbit anti-HRP, prepared as in Example 1, Part A, as described in Example 1, Part C.

The yield of the desired hybrid antibody in such a synthesis is expected to approach 90%, since the formation of the reduced anti-glucose oxidase by this S-sulfonation route has a yield of approximately 90%.

EXAMPLE 6

Synthesis of Half-Molecules from Monoclonal Antibodies

S-sulfonated half-molecules were prepared and characterized as described in Example 1, Part A, using monoclonal antibodies. The yield of the desired S-sulfonated half-molecule was 100%. The monoclonal antibodies were anti-theophylline (heavy chain subclass $\gamma_1$ and light chain isotype κ) and anti-digoxin (heavy chain subclass $\gamma_3$ and light chain isotype κ). The starting material monoclonal antibodies were affinity purified from ascites fluid, concentrated by ultrafiltration to a concentration of 2 mg/mL, and typed as to light chain isotype and heavy chain subclass by double diffusion in agar gel.

I claim:

1. A substantially pure immunoglobulin heavy chain-light chain half-molecule having the structure R—S—X, where R is $H_1L_1$ and X is $SO_3^-$.

2. The immunoglobulin half-molecule of claim 1 having antigen-binding specificity for glucose oxidase.

3. The immunoglobulin half-molecule of claim 1 having antigen-binding specificity for horseradish peroxidase.

4. The immunoglobulin half-molecule of claim 1 having antigen-binding specificity for digoxin, wherein the half-molecule is obtained from monoclonal antibody to digoxin.

5. The immunoglobulin half-molecule of claim 1 having antigen-binding specificity for theophylline, wherein the half-molecule is obtained from monoclonal antibody to theophylline.

6. A process for preparing S-sulfonated immunoglobulin half-molecules by selectively cleaving an immunoglobulin molecule into its heavy chain-light half-molecules by sulfitolysis of the interheavy chain disulfide linkage; wherein the sulfitolysis reaction comprises the steps of:
    (A) mixing an immunoglobulin molecule with sodium sulfite and 5,5'-dithiobis(2-nitrobenzoic acid);
    (B) incubating in a nonoxidizing atmosphere; and
    (C) separating the protein products.

7. A process for preparing reduced immunoglobulin half-molecules by selectively cleaving an immunoglobulin molecule into its heavy chain-light chain half-molecules by sulfitolysis of the inter-heavy chain disulfide linkage followed by reduction of the S-sulfonated half-molecules wherein the sulfitolysis reaction comprises the steps of:
    (A) mixing an immunoglobulin molecule with sodium sulfite and 5,5'-dithiobis(2-nitrobenzoic acid);
    (B) incubating in a nonoxidizing atmosphere; and
    (C) separating the protein products.

8. The process of claim 7 wherein the reduction step utilizes a thiol-containing reagent.

9. The process of claim 8 wherein the thiol-containing reagent is selected from the group consisting of β-mercaptoethanol, dithiothreitol and β-mercaptoethylamine.

10. The process of claims 7, 8 or 9 carried out in a nonoxidizing atmosphere and in the presence of alkali earth metal salts.

11. A process for preparing reduced immunoglobulin half-molecules by selectively cleaving an immunoglobulin molecule into its heavy chain-light chain half-molecules by reduction of the inter-heavy chain disulfide linkage; wherein the immunoglobulin molecule is bound to an immobilized receptor.

12. The process of claim 11 wherein the receptor is an antigen bonded to a support.

13. The process of claim 11 wherein the receptor is Protein A bonded to a support.

14. The process of claims 11, 12 or 13 wherein the reduction step utilizes a thiol-containing reagent.

15. The process of claim 14 wherein the thiol-containing reagent is selected from the group consisting of β-mercaptoethanol, dithiothreitol and β-mercaptoethylamine.

* * * * *